United States Patent [19]
Villanueva

[11] Patent Number: 5,938,641
[45] Date of Patent: Aug. 17, 1999

[54] SAFETY SYRINGE

[76] Inventor: George Villanueva, 695 E. 163rd St., Apt. 4F, Bronx, N.Y. 10456

[21] Appl. No.: 09/004,038

[22] Filed: Jan. 7, 1998

[51] Int. Cl.$^6$ ..................................................... A61M 5/32
[52] U.S. Cl. ........................... 604/195; 604/110; 604/243
[58] Field of Search ..................................... 604/110, 195, 604/192, 194, 198, 227, 228, 229, 240, 243

[56] References Cited

U.S. PATENT DOCUMENTS

| | | |
|---|---|---|
| 2,722,215 | 11/1955 | Dahlgren . |
| 3,306,290 | 2/1967 | Weltman . |
| 4,026,287 | 5/1977 | Haller . |
| 4,747,829 | 5/1988 | Jacob et al. . |
| 4,747,831 | 5/1988 | Kulli . |
| 4,767,413 | 8/1988 | Haber et al. . |
| 4,946,446 | 8/1990 | Vadher . |
| 4,955,870 | 9/1990 | Ridderheim et al. . |
| 4,966,593 | 10/1990 | Lennox . |
| 4,988,339 | 1/1991 | Vadher . |
| 4,994,034 | 2/1991 | Botich et al. . |
| 5,084,029 | 1/1992 | Tagliaferri et al. . |
| 5,114,404 | 5/1992 | Paxton et al. . |
| 5,147,303 | 9/1992 | Martin . |
| 5,188,599 | 2/1993 | Botich et al. . |
| 5,190,526 | 3/1993 | Murray et al. ....................... 604/195 X |
| 5,222,944 | 6/1993 | Harris . |
| 5,267,976 | 12/1993 | Guerineau et al. . |
| 5,328,475 | 7/1994 | Chen ....................................... 604/195 |
| 5,342,308 | 8/1994 | Boschetti . |
| 5,344,405 | 9/1994 | Richards . |
| 5,484,414 | 1/1996 | Pace . |
| 5,542,927 | 8/1996 | Thorne et al. . |
| 5,772,687 | 6/1998 | Saito .................................... 604/110 X |

Primary Examiner—Ronald Stright
Assistant Examiner—A. T. Nguyen
Attorney, Agent, or Firm—Steven Horowitz

[57] ABSTRACT

Needle housing of simple springless syringe retracts into casing tube's barrel after use to avoid accidental needle sticks. A lip at the barrel's forward end and a far end of a rim of the needle housing together form a partial forward end wall. The plunger's plug is sealably and frangibly attached at forward end of plunger to interior portion of plunger and to an arm running lengthwise through plunger. An injection needle housing has a rim bonded to the exterior of the forward end of the syringe barrel, a projecting needle for injecting the fluid, an interior female cavity whose walls are shaped to sealably receive and lock the plug after the plug leaves the barrel during injection and a stabilizing lip containing breakaway points whose lower and upper portions are on each side of the partial forward end wall of the barrel. After injection of the fluid through the needle by pushing down on the plunger, a further push on the plunger causes the plug to breaks away from the plunger at breakaway points, leave the barrel and snugly lock into interior female cavity of needle housing. To retract the entire needle housing including a portion of a lip of the needle housing that breaks away with it, user manually pulls back on the plunger. After retraction, forward wall of barrel is not completely open to lessen chance of needle falling out of barrel and stick someone if it dislodges from its housing or from plug.

2 Claims, 3 Drawing Sheets

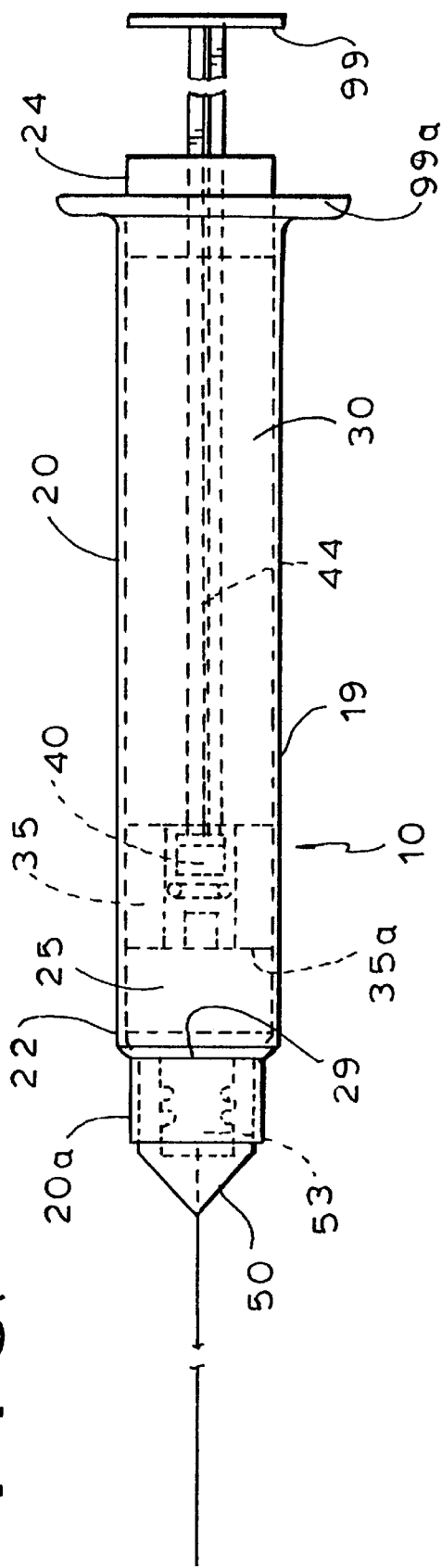

SAFETY SYRINGE

This invention relates to hypodermic needles and particularly to needles having a retractable feature for safety reasons.

There is no hypodermic needle currently on the market that completely and satisfactorily solves the safety problem from accidentally pricking after their use and thereby contaminating the medical worker with microorganisms or blood on the needle. The prior art attempts to solve this problem suffer from the defect that they are either too complicated to be sufficiently practical, which makes the syringe to costly to manufacture and market on a mass scale, or else do not completely solve the problem.

For example, most of the prior art retractable syringe systems that attempt to solve the problem are complicated in that they contain springs. This greatly adds to the cost of manufacture and has resulted in the absence of a hypodermic syringe in hospitals in this country equipped with the retractability feature. Current medical practice in hospitals remains that of removing the needle from the patient and then disposing of it. But in doing so the needle is exposed.

For example, U.S. Pat. No. 4,994,034 to Botich et al. discloses a hypodermic injection system with a retractable needle wherein the needle retracts within the interior cavity of a syringe plunger utilizes a coiled spring.

Other prior art have other drawbacks. For example, U.S. Pat. No. 4,026,287 to Haller discloses a syringe having a barrel and a piston actuated plunger reciprocable therein with means to retract the cannula after dispensing fluid. The plunger engages the forward end wall of the syringe barrel and the end wall of the barrel breaks away during retraction to allow the cannula, which is attached to the plunger, to be retracted back into the barrel. After retraction, however, while the cannula or needle is encased in the syringe barrel, the syringe barrel is entirely open on one side. That is, the end wall of the barrel that had broken away no longer covers one end of the barrel, the end that the sharp point of the cannula or needle is facing. Therefore, if the needle or cannula were to dislodge from the needle housing, or if the needle and needle housing were to dislodge from the plunger, the sharp point of the cannula or needle could unexpectedly fall out of the syringe barrel, even after retraction, and prick or contaminate a medical worker.

Another problem with the syringe of Haller is that in the main embodiment the plunger rod must be advanced and rotated in order to engage the recess in the end wall and then be in a position to retract. Even in the alternative embodiment where no rotation is necessary, the plunger is not as securely engaged to the end wall as would be necessary to be confident that the needle cannot be dislodged from the plunger. Moreover, both in the main embodiment and in the alternative embodiment the plunger is exposed at all times and the end wall that it locks into is also exposed at all times even prior to use. This is unsanitary and it also allows the possibility of the plunger's form being disturbed prior to use and prior to the syringe being filled with liquid.

The prevent invention solves these problems by devising a simple yet effective system for retraction of the needle after use into an essentially closed barrel and wherein the breakaway part is insulated inside the plunger prior to use.

OBJECTS AND ADVANTAGES

The following important objects and advantages of the present invention are:

(a) to provide a syringe with a retractable needle,
(b) to provide a syringe in which medical workers need not fear contamination by accidental pricking after using the syringe,
(c) to provide a syringe that is safe and effective yet simple enough that the cost of manufacturing is still very low,
(d) to provide a syringe in which after retraction of the needle into the syringe barrel, the needle is encased in the barrel safely and the barrel has no fully open end through which the needle, if it were to dislodge from its housing or from the plug, could slip out of the barrel and accidentally prick someone,
(e) to provide a syringe in which the needle housing has a rim bonded to the exterior of the partial forward end of the syringe barrel on its far mostly open end,
(f) to provide a retractable syringe in which, during injection phase, a plug insulated in the plunger breaks away from the plunger at breakaway points that seal the bottom of the plunger from passage of any liquid and is ready for engagement with the inside of the needle housing.

These objects and advantages as well as all the features of the present invention will be further understood when reference is made to the following drawings illustrating the invention.

BRIEF DESCRIPTION OF THE DRAWINGS

FIG. 1 is a side elevational view of the syringe of the present invention filled with liquid with the plunger pushing through the barrel tube (prior to injection).

FIG. 2 is a side elevational view of the syringe of the present invention filled with liquid with the plug partially traversing the bottom of the barrel and entering the needle housing.

DETAILED DESCRIPTION OF THE DRAWINGS

As seen in FIGS. 1–7, the syringe of the present invention is exceedingly simple yet has the advantage of being fully retractable into a position so that it cannot fall back out of the barrel if the needle dislodges from the plunger, as will be further described.

Figure 3:
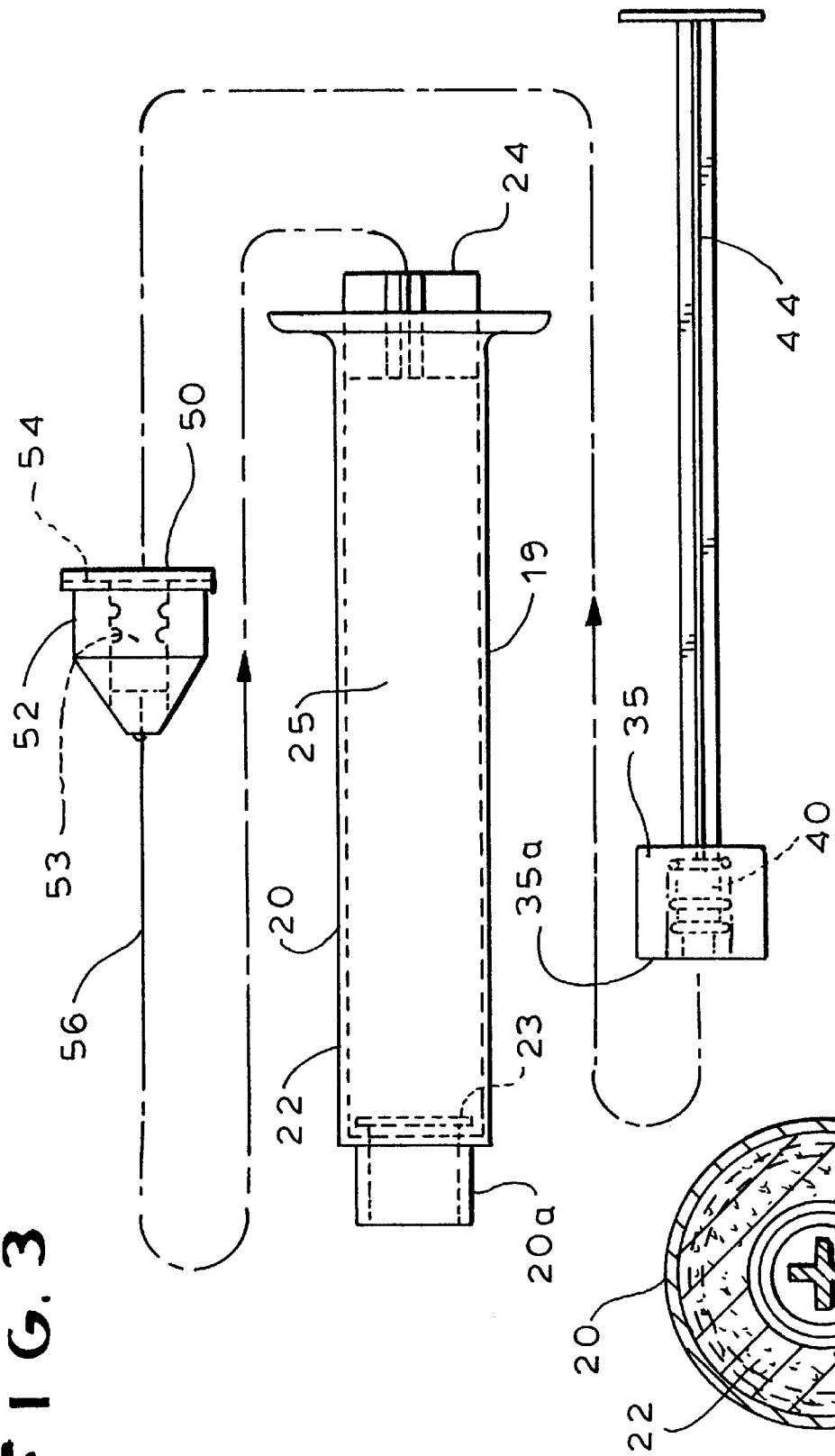
FIG. 3 is an exploded view of the separate parts of the syringe system of the present invention including barrel, arm and plug, plunger and needle housing.

The parts of syringe 10 are displayed in FIG. 3, which is an exploded view of the separate parts of the syringe system of the present invention including barrel, arm and plug, plunger and needle housing. The main part of syringe 10 is a standard plastic casing tube 19 for containing and discharging fluid made up of hollow syringe barrel 20 and a nose 20a jutting therefrom. The main purpose of nose 20a is so that it is possible for needle housing 50 to attach to the casing tube 19. The precise configuration of such attachment is not essential to this invention. Syringe barrel 20 is hollow. Barrel 20 is usually although not necessarily cylindrical and has a forward end 22, a rear end 24 and an internal chamber 25 for containing fluid. As seen in the enlarged fragmentary views of FIGS. 4–6, forward end 22 is essentially a partial wall 23 or lip leaving opening 29. In its simplest form, opening 29 is preferably in the center of partial forward wall 23 but it is contemplated that in certain embodiments it may be located at other points.

The syringe 10 of the present invention also contains a standard plunger 30 that is shaped to fit snugly inside hollow barrel 20 and slide through the barrel 20 from an initial position near the rear end 24 of barrel 20 toward partial forward wall 23 when a handle 99 external to and connected to the barrel 20 is pressed in one prolonged push. The syringe plunger 30 contains a plug 40 frangibly attached to an interior portion 35 of plunger 30 at a forward end 35a of the plunger 30. Plunger 30 is sized to be snugly fitted within and slide through said syringe barrel 20.

An arm 44 running lengthwise through the plunger 30 is attached to plug 40 at one side thereof distal to the forward end 35a of plunger 30 (and distal to the forward end 22 of barrel 20) and is used to push the plunger 30 and with it the fluid in the barrel 20 out of the barrel 20. This of course has the effect of also pushing plug 40 toward opening 29. Arm 44 is longer, approximately half an inch longer, than would be necessary to accomplish the limited purpose of pushing plug 40 merely to the forward end 22 of barrel 20 but since the plug 40 is attached to the plunger 30 the plug 40 cannot travel further than the plunger 30 travels, (the plunger 30 will have travelled to the forward end 22 of barrel 20) upon a mere single prolonged pressing of the handle 99. After the plunger 30 has reached the forward end 22 of the barrel 20, however, upon a second pressing of the handle 99, plug 40 will enter and traverse opening 29 and enter the needle housing 50, as explained below.

Figure 4:
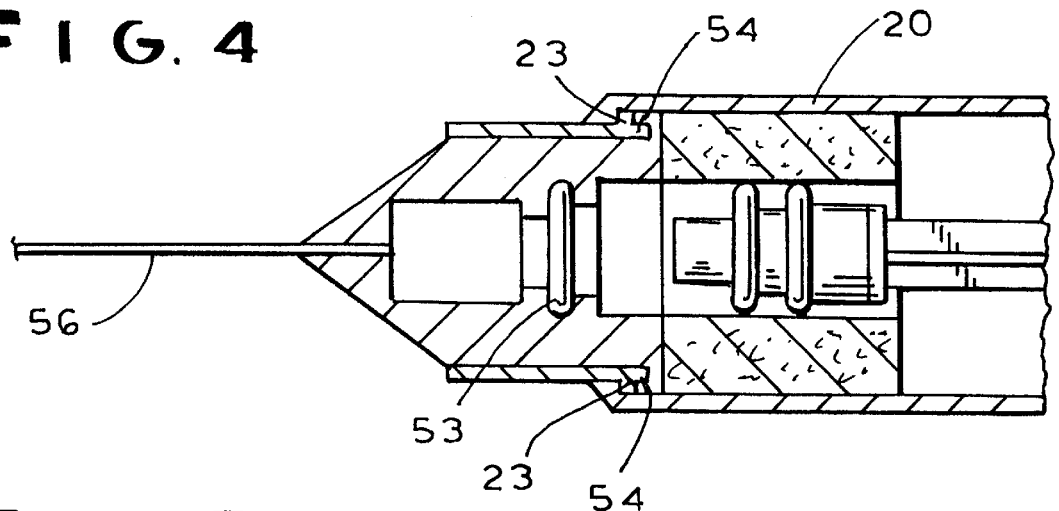
FIG. 4 is an enlarged fragmentary cross-sectional view of the syringe of the present invention in condition wherein the plunger has reached the forward end of the barrel.
Figure 5:
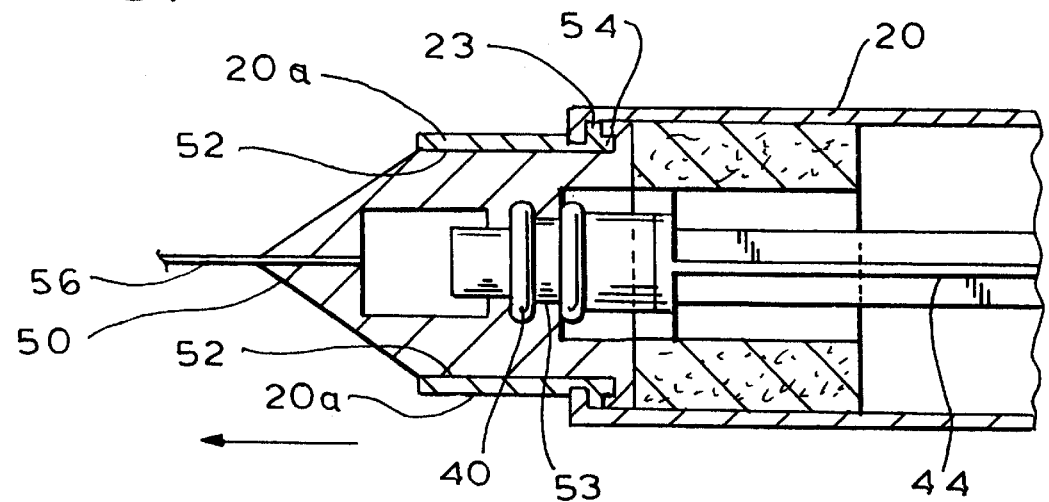
FIG. 5 is an enlarged fragmentary cross-sectional view of the syringe of the present invention after the plug has locked into the needle housing during injection.

As best seen in FIGS. 1–3, in order for plug 40 to traverse opening 29 and enter needle housing 50, the plug 40 must first break away from the interior portion 35 of plunger 30 at the forward end 35a of plunger 30. Plug 40 is able to break away because plug 40 is only frangibly attached to the interior portion 35 of plunger 30 at the forward end 35a of plunger 30. Accordingly, when the plunger 30 is pushed down as a result of pressure on the external handle 99 (the force of which is being pushed against member 99a), plunger 30 slides through barrel 20 until the forward end 22 of barrel 20, as seen in FIGS. 2 and 4. When the plunger 30 is pushed down a second time, the additional force causes plug 40 to break away from the plunger 30, as seen in FIG. 5.

At all times prior to breaking away (see FIGS. 1, 2), plug 40 is tightly sealed to plunger 30 in a sanitary and safe manner. Plug 40 breaks away from plunger 30 at breakaway points that seal the bottom of the plunger from passage of any liquid.

As seen in FIG. 3, needle housing 50 consists essentially of an outer shell 52 surrounding the interior female cavity 53 shaped to receive plug 40, a rim 54 that frangibly bonds to both sides of the lip 23 of partial end wall 22 of barrel 20 and the actual needle 56 projecting outward from outer shell 52. Plug 40 is shaped so as to mate with and lock into interior female cavity 53 of needle housing 50 when plug 40 enters needle housing 50 after it traverses opening 29. Plug 40 is flexible enough to enter and mate with interior female cavity 53 of needle housing 50 but once engaged in the interior female cavity 53 plug 40 cannot be dislodged from it since it fits snugly therein.

After plug 40 engages interior female cavity 53 of needle housing 50 and the fluid in the barrel has been discharged through the needle 56 into a human body, the vacuum in barrel 20 unleashes a force pushing plunger 30 toward the rear end of barrel 20.

To retract the entire needle housing 50 including a portion of its rim 59 that breaks away with it, user manually pulls back on the plunger by pulling against external handle 99.

Figure 6:
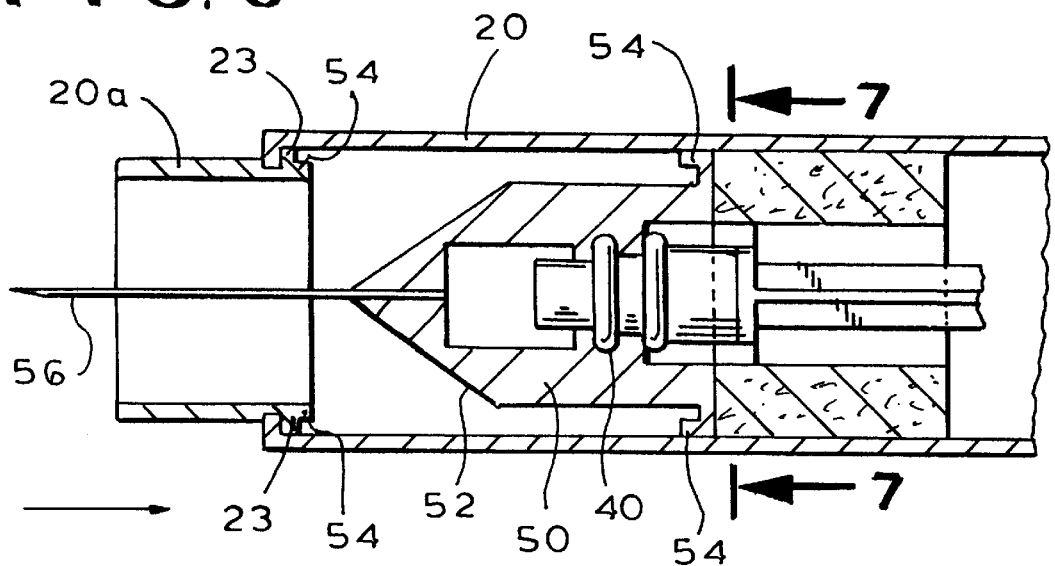
FIG. 6 is an enlarged fragmentary cross-sectional view of the syringe of the present invention after retraction.

The force of the plunger retracting into the barrel 20 causes the plug 40, together with the entire needle housing 50 which it is locked together with, to retract into barrel 20. As best seen in FIG. 6, the needle housing simultaneously pushes the plunger upward into the barrel.

Figure 7:
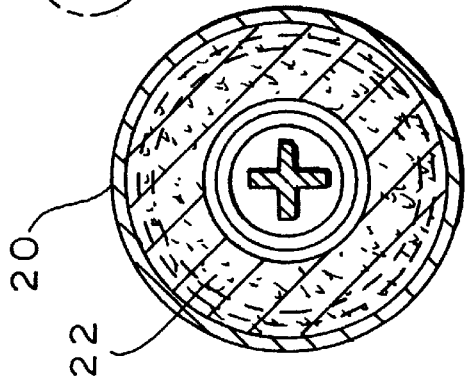
FIG. 7 is cross-sectional view of the syringe taken along line 7—7 of FIG. 6.

When needle housing 50 retracts, rim 59 breaks away partially. This means that a part of the rim 59 remains attached to lip 23 while a part of rim 59 remains attached to needle housing 50 and retracts into the barrel 20. As a result, as best seen in FIG. 7, after retraction barrel 20 retains a partial end wall 22 (that has been widened by part of rim 59) to more safely contain the needle after retraction.

For example, after retraction, plunger 20, plug 40 and interior cavity 53 of needle housing 50 are all located safely within barrel 20. After retraction, barrel 20 is not entirely open on its partial forward end 22. Lip 23 of forward end 22 combined with rim 54 form a partial wall on the forward end of barrel 20. Accordingly, if after retraction of the interior female cavity 53 of needle housing 50 and plug 40 into barrel 20, needle 56 were to dislodge from interior female cavity 53 of needle housing 50 or alternatively if interior female cavity 53 were somehow to dislodge from plug 40, the needle 56 could still not easily fall out of barrel 20. This is an advantage over retractable syringe systems wherein the needle is retracted into a syringe barrel that is entirely open on one end.

It is to be understood that while the apparatus of this invention have been described and illustrated in detail, the above-described embodiments are simply illustrative of the principles of the invention. It is to be understood also that various other modifications and changes may be devised by those skilled in the art which will embody the principles of the invention and fall within the spirit and scope thereof. It is not desired to limit the invention to the exact construction and operation shown and described. The spirit and scope of this invention are limited only by the spirit and scope of the following claims.

What is claimed is:

1. A retractable syringe comprising:

a casing tube for containing and discharging fluid, the tube having a nose and a hollow barrel, the barrel having a forward end and a rear end, said forward end comprising a lip surrounding a central opening, a plunger sized to be snugly fitted within and slide through said hollow barrel and containing a plug, said plug prior to injection being sealably and frangibly attached to an interior portion of the plunger at a forward end of the plunger and being attached to an arm running lengthwise through said plunger, and a needle housing made of an outer shell surrounding an interior female cavity shaped to sealably receive the plug after the plug traverses the central opening during injection, and having a rim frangibly bonded to the forward end of the barrel and a needle projecting from the outer shell for injecting fluid, said casing tube having a handle connected thereto so that one prolonged push on said handle causes a plunger to slide through the barrel, whereupon a second push on the handle causes said plug to break away from the interior portion of the plunger and lock into the interior female cavity of the needle housing, and wherein pulling back on the plunger after injection causes the needle housing and the plug to retract into the barrel toward the rear end thereof together with the plunger so that the needle remains lodged safely at the rear end of the barrel.

2. The syringe of claim 1, wherein the rim partially breaks away during retraction and combines with the lip to form a partial wall on the forward end of the barrel to more safely contain the needle after retraction.

* * * * *